US010265012B2

(12) United States Patent
Levanon

(10) Patent No.: US 10,265,012 B2
(45) Date of Patent: Apr. 23, 2019

(54) METHOD AND SYSTEM FOR DETERMINING A PRE-MULTISYSTEM FAILURE CONDITION USING TIME INTEGRATED VOICE ANALYSIS

(71) Applicant: BEYOND VERBAL COMMUNICATION LTD, Tel-Aviv (IL)

(72) Inventor: Yoram Levanon, Ramat Hasharon (IL)

(73) Assignee: BEYOND VERBAL COMMUNICATION LTD., Tel-Aviv (IL)

( * ) Notice: Subject to any disclaimer, the term of this patent is extended or adjusted under 35 U.S.C. 154(b) by 371 days.

(21) Appl. No.: 14/892,212

(22) PCT Filed: May 18, 2014

(86) PCT No.: PCT/IL2014/050430
§ 371 (c)(1),
(2) Date: Nov. 19, 2015

(87) PCT Pub. No.: WO2014/188408
PCT Pub. Date: Nov. 27, 2014

(65) Prior Publication Data
US 2016/0095545 A1    Apr. 7, 2016

Related U.S. Application Data

(60) Provisional application No. 61/825,105, filed on May 20, 2013.

(51) Int. Cl.
A61B 5/00   (2006.01)
A61B 5/02   (2006.01)
A61B 7/00   (2006.01)

(52) U.S. Cl.
CPC ........ *A61B 5/4803* (2013.01); *A61B 5/02028* (2013.01); *A61B 5/4064* (2013.01); *A61B 5/7275* (2013.01); *A61B 7/00* (2013.01)

(58) Field of Classification Search
CPC .. A61B 5/4803; A61B 5/02014; A61B 5/7275
See application file for complete search history.

(56) References Cited

U.S. PATENT DOCUMENTS

2009/0163779 A1    6/2009   Dean

FOREIGN PATENT DOCUMENTS

| EP | 2411804 | 8/2015 |
| WO | WO/2010/123483 | 10/2010 |
| WO | WO/2012/138740 | 10/2012 |
| WO | WO/2014/188408 | 11/2014 |

OTHER PUBLICATIONS

International Search Report of PCT/IL2014/050430, dated May 18, 2014.

*Primary Examiner* — William H Matthews

(57) ABSTRACT

A method for diagnosing an impending multisystem failure in a patient, comprising steps of obtaining data of recorded speech of the patient, calculating an intensity function of the data across a plurality of frequencies, and determining the number of vibrations in the range of an octave in the recorded speech. A number of vibrations larger than four are indicative of an impending multisystem failure in the patient.

38 Claims, 4 Drawing Sheets

METHOD AND SYSTEM FOR DETERMINING A PRE-MULTISYSTEM FAILURE CONDITION USING TIME INTEGRATED VOICE ANALYSIS

FIELD OF THE INVENTION

The invention relates to a system and a method for determining pre-multisystem failure conditions. More specifically, the invention relates to a system that analyzes the speech of a patient and predicts whether they are expected an impending multisystem failure or a long term expected multisystem failure.

BACKGROUND

Multisystem failure is altered organ function in an acutely ill patient requiring medical intervention to achieve homeostasis.

Stroke, or cerebrovascular accident (CVA), is one of the most common multisystem failures. It is the rapid loss of brain function due to disturbance in the blood supply to the brain. This can be due to ischemia (lack of blood flow) caused by blockage (thrombosis, arterial embolism), or a hemorrhage. As a result, the affected area of the brain cannot function, which might result in an inability to move one or more limbs on one side of the body, inability to understand or formulate speech, or an inability to see one side of the visual field.

The symptoms of stroke usually appear suddenly. Initially the person may feel sick, and look pale and very unwell. They may complain of a sudden headache. They may have sudden numbness in their face or limbs, particularly down one side of their body. They may appear confused and have trouble talking or understanding what is being said to them. They may have vision problems, and trouble walking or keeping their balance. Sometimes a seizure (fit) or loss of consciousness occurs. Once these symptoms appear, it is inevitable to prevent the stroke from happening and the patient will be treated as a stroke patient.

Many efforts are invested in finding precursors predicting the appearance of stroke days, weeks and maybe months before it actually happens. For example, Patent Application WO12138740A2 suggests a predictive model which can be used to predict an individual's propensity for developing a given disease like stroke. Patent Application EP 2411804 suggests a method for early in vitro diagnosis of stroke by identifying certain biological markers. These methods are useful for detection a few hours before the onset of the stroke but not earlier than that.

Currently, there are no symptoms that predict a long time ahead (couple of day to few weeks) whether a person is about to have a stroke. Therefore, there is a long felt need for a system and a method that will predict early enough a stroke that will enable efficient treatment for prevention.

SUMMARY

It is one object of the present invention to provide a method for diagnosing an impending multisystem failure in a patient, comprising steps of: (a) obtaining data of recorded speech of the patient; (b) calculating an intensity function of the data across a plurality of frequencies; and (c) determining the number of vibrations in the range of an octave in the recorded speech; wherein the number of vibrations are larger than four is indicative of the impending multisystem failure in the patient.

It is another object of the present invention to provide the system as defined above, wherein said multisystem failure is caused by a stroke.

It is another object of the present invention to provide the system as defined above, additionally comprising a step of defining the vibration as at least 10% difference in the intensity throughout no more 25 Hz.

It is another object of the present invention to provide the system as defined above, wherein additionally comprising a step of determining the octave to be analyzed from a group consisting of: (a) octave between 220-440 Hz; (b) octave between 280-560 Hz; and any combination thereof.

It is another object of the present invention to provide the system as defined above, wherein more than three vibrations per the octave are also indicative of the upcoming multisystem failure; the vibrations have a steep slope; said steep slope is about 30%.

It is another object of the present invention to provide the system as defined above, wherein the recorded speech is at least 15 seconds long.

It is another object of the present invention to provide the system as defined above, additionally comprising a step of selecting the intensity function from a group consisting of: (a) average intensity function; (b) maximum intensity function; and any combination thereof.

It is another object of the present invention to provide the system as defined above, wherein searching the crater feature in a way selected from a group consisting of: (a) manually; (b) automatically; and any combination thereof.

It is another object of the present invention to provide the system as defined above, additionally comprising a step of graphically plotting the intensity function.

It is another object of the present invention to provide a method for predicting a long term expected multisystem failure in a patient, comprising steps of: (a) obtaining data of recorded speech of the patient; (b) calculating an intensity function of the data across a plurality of frequencies; and (c) searching for at least one crater feature in the intensity function; wherein the method additionally comprising step of: (d) diagnosing the patient with a long term expected multisystem failure according to identification of said at least one crater feature in step (c).

It is another object of the present invention to provide the method as defined above, It is another object of the present invention to provide the system as defined above, wherein said multisystem failure is caused by a stroke.

It is another object of the present invention to provide the method as defined above, wherein the crater feature depth is over 30%.

It is another object of the present invention to provide the method as defined above, wherein said crater feature appears in a location in the range of 140-180 Hz and 280-360 Hz.

It is another object of the present invention to provide the method as defined above, wherein the crater feature has a horizontal base in the range of 180-250 Hz.

It is another object of the present invention to provide the method as defined above, wherein the recorded speech is at least 15 seconds long. It is important that the audible data will include at least 15 second speech of the person to be diagnosed. Shorter segments of speech are also possible but the longer the speech segment the analysis is more accurate.

It is another object of the present invention to provide the method as defined above, wherein additionally comprising a step of selecting the intensity function from a group consisting of: (a) average intensity function; (b) maximum intensity function; and any combination thereof.

It is another object of the present invention to provide the method as defined above, wherein searching the crater feature in a way selected from a group consisting of: (a) manually; (b) automatically; and any combination thereof.

It is another object of the present invention to provide the method as defined above, additionally comprising a step of graphically plotting the intensity function.

It is another object of the present invention to provide a system for diagnosing a patient for an expected multisystem failure in a patient, comprising: (a) audible data of the patient's speech (b) at least one input apparatus, adapted to receive the audible data; (c) at least one processing apparatus adapted to transfer the audible data to numerical data; the numerical data contains: (i) frequency of the audible data as a function of time; and (ii) the frequency's intensity; and (d) at least one calculating apparatus adapted to calculate a frequency function from the numerical data; wherein more than 4 vibrations in an octave in the frequency function is predictable of an impending multisystem failure.

It is another object of the present invention to provide the system as defined above, wherein said multisystem failure is caused by a stroke.

It is another object of the present invention to provide the system as defined above, additionally comprising at least one output apparatus adapted to provide a graphical presentation of said frequency function.

It is another object of the present invention to provide the system as defined above, wherein the vibration is defined as at least 10% difference in the intensity throughout no more 25 Hz.

It is another object of the present invention to provide the system as defined above, wherein the octaves to be analyzed are selected from a group consisting of: (a) octave between 220-440 Hz; (b) octave between 280-560 Hz; and any combination thereof.

It is another object of the present invention to provide the system as defined above, wherein more than three vibrations per octave are also indicative of an upcoming multisystem failure; the vibrations have a steep slope; said steep slope is about 30%.

In yet another embodiment of the invention, wherein the recorded speech is at least 15 seconds long.

It is another object of the present invention to provide the system as defined above, wherein the intensity function is selected from a group consisting of: (a) average intensity function; (b) maximum intensity function; and any combination thereof.

It is another object of the present invention to provide the system as defined above, wherein at least one input apparatus, at least one processing apparatus, at least one calculating apparatus, at least one output apparatus comprises at least one computer software and at least one computer hardware.

It is another object of the present invention to provide the system as defined above, additionally comprising at least one output apparatus additionally comprising an analyzing apparatus; the apparatus is adapted to determine according to the graphical presentation whether the patient is suspected to have a multisystem failure in the short or long term.

It is another object of the present invention to provide the system as defined above, additionally comprising at least one plotting apparatus adapted to graphically plot the intensity function.

It is another object of the present invention to provide the system as defined above, additionally comprising at least one recognition apparatus, adapted to recognize more than 4 vibrations in an octave.

It is another object of the present invention to provide a system for diagnosing a patient for an expected multisystem failure in a patient, comprising: (a) audible data of the patient's speech; (b) at least one input apparatus, adapted to receive the audible data; (c) at least one processing apparatus adapted to transfer the audible data to numerical data; the numerical data contains: (i) frequency of the audible data as a function of time; and (ii) the frequency's intensity; and (d) at least one calculating apparatus adapted to calculate a frequency function from the numerical data; wherein a crater in the frequency function is predictable of a long term expected multisystem failure.

It is another object of the present invention to provide the system as defined above, wherein said multisystem failure is caused by a stroke.

It is another object of the present invention to provide the system as defined above, additionally comprising at least one output apparatus adapted to provide a graphical presentation of the frequency function.

It is another object of the present invention to provide the system as defined above, wherein the crater feature depth is over 30%.

It is another object of the present invention to provide the system as defined above, wherein the recorded speech is at least 15 seconds long.

It is another object of the present invention to provide the system as defined above, wherein additionally comprising a step of selecting the intensity function from a group consisting of: (a) average intensity function; (b) maximum intensity function; and any combination thereof.

It is another object of the present invention to provide the system as defined above, wherein the at least one input apparatus, at least one processing apparatus, at least one calculating apparatus, at least one output apparatus comprises at least one computer software and at least one computer hardware.

It is another object of the present invention to provide the system as defined above, wherein the crater feature appears in a location in the range of 140-180 Hz; and 280-360 Hz.

It is another object of the present invention to provide the system as defined above, wherein the crater feature has a horizontal base in the range of 180-250 Hz.

It is another object of the present invention to provide the system as defined above, additionally comprising at least one output apparatus; the apparatus is adapted to determine whether the patient is suspected to have a multisystem failure in the long term.

It is another object of the present invention to provide the system as defined above, additionally comprising at least one plotting apparatus adapted to graphically plot the intensity function.

BRIEF DESCRIPTION OF THE FIGURES

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured. In the accompanying drawing:

DETAILED DESCRIPTION OF THE INVENTION

Figure 1:
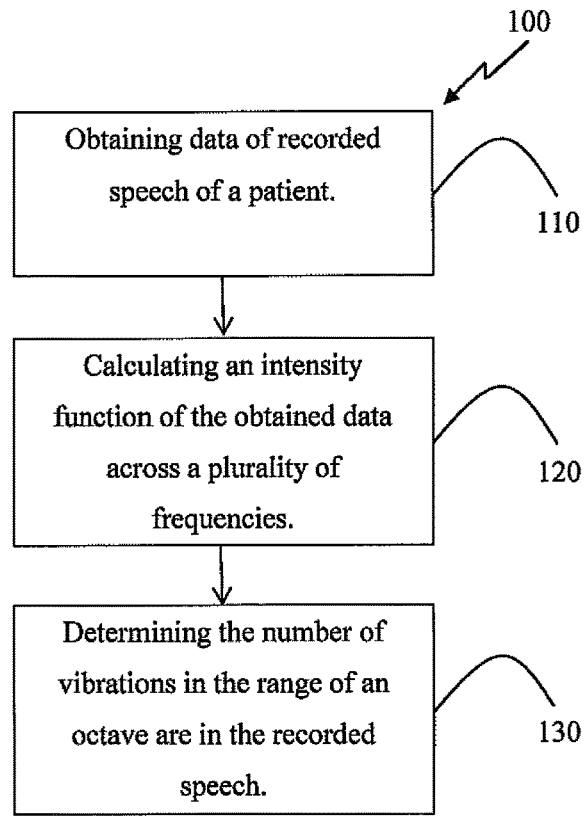
FIG. 1 is a schematic flow diagram illustrating the method for diagnosing an impending multisystem failure in a patient (100)

The following description is provided, alongside all chapters of the present invention, so as to enable any person skilled in the art to make use of the invention and set forth the best modes contemplated by the inventor of carrying out this invention. Various modifications, however, will remain apparent to those skilled in the art, since the generic principles of the present invention is defined to specifically provide a system and method for diagnosing an impending and a long term expected multisystem failure.

The term "crater feature" refers hereinafter to a shape (on a graph of frequency vs. intensity) which manifests as a sharp drop at a first frequency continued by a relatively low level along approximately 50 Hz or more and then a relatively steep rise at a second frequency.

The term "multisystem failure" refers hereinafter to altered organ function in an acutely ill patient requiring medical intervention to achieve homeostasis. Multisystem failure can be caused by stroke, an aggressive infection, sepsis, cancer etc.

The term "impending multisystem failure" refers hereinafter to a multisystem failure expected to happen in time period of few hours to few days.

The term "long-term expected multisystem failure" refers hereinafter to a stroke expected to happen in time period of few weeks.

The term "stroke" refers herein after to the rapid loss of brain function due to disturbance in the blood supply to the brain due to ischemia (lack of blood flow) caused by blockage (thrombosis, arterial embolism), or a hemorrhage.

The term "octave" refers herein after to the interval between one musical pitch and another with half or double its frequency.

The term "average intensity function", refers herein after to a function calculated across the plurality of frequencies by averaging, at each of the plurality of frequencies, a plurality of sample intensity values of the speech. In one example the average intensity function may be computed by measuring the intensity of the speaker's voice during the time period "T" (in one example, T may be a relatively short span of a few dozen seconds). The average voice intensity is measured by measuring the intensities of sound at each different frequency, in the frequency range of between, for example, 20 Hz and 15000 Hz, during multiple time-points within the range T. The time-points (T1) may be selected to be equally distributed during the total range T. At each time-point, the intensity of each frequency is measured and is described as a function "F1" of that frequency I (F1, T1). This measurement is repeated at every time-point for a total of "N" measurements to span the entire range T. Thus, in this example, the average intensity function for each frequency can be described as:

$$I(f0) = 1/n \; \Sigma ni = I(f0, T1)$$

The term "maximum intensity function", refers herein after to a function calculated across the plurality of frequencies by determining, at each of the plurality of frequencies, a maximum of a plurality of sample intensity values of the speech. In one example essentially the same voice intensity measurements that were described for the average intensity function may be collected. In this example, the maximum intensity function will be arrived at (during the time T) by the equation:

$$IMAX(f0) = MAX[I(f0, T)]$$

The present invention provides a method for diagnosing an impending multisystem failure in a patient, comprising steps of: (a) obtaining data of recorded speech of the patient; (b) calculating an intensity function of the data across a plurality of frequencies; and (c) determining the number of vibrations in the range of an octave in the recorded speech; wherein the number of vibrations are larger than four is indicative of the impending multisystem failure in the patient.

In yet another embodiment of the invention, wherein said multisystem failure is caused by a stroke.

The data may be recorded on a tape, a CD or any type of digital media like a computer, smart-phone or a tablet. A professional recording in a studio with no interruptions background noise is preferable but also a simple home recording in a quite environment will be sufficient for the analysis.

In yet another embodiment of the invention, additionally comprising a step of defining the vibration as at least 10% difference in the intensity throughout no more 25 Hz.

The intensity in the intensity function is a normalized intensity and 100% is defined as the highest intensity identified. All other intensities are in accordance with the highest intensity defined as 100%.

In yet another embodiment of the invention, wherein additionally comprising a step of determining the octave to be analyzed from a group consisting of: (a) octave between 220-440 Hz; (b) octave between 280-560 Hz; and any combination thereof.

More than four vibrations in a different octave may also be indicative of an impending multisystem failure. These two octaves mentioned are the most common to show the mentioned vibrations.

The greater the number of vibrations are in an octave the greater is the chance for an impending multisystem failure and the closer the event is. Usually the number of vibrations is 5-6 but might be greater in extreme conditions.

In yet another embodiment of the invention, wherein more than three vibrations per the octave are also indicative of the upcoming multisystem failure; the vibrations have a steep slope; said steep slope is about 30%.

Less than five vibrations may also indicate of an impending multisystem failure but then their slope must be steeper. A steep slope relates to a slope with an angle greater than 30°. However, less than four vibrations are not indicative of an impending multisystem failure.

In yet another embodiment of the invention, wherein the recorded speech is at least 15 seconds long.

It is important that the audible data will include at least 15 second speech of the person to be diagnosed. Shorter segments of speech are also possible but the longer the speech segment the analysis is more accurate.

In yet another embodiment of the invention, additionally comprising a step of selecting the intensity function from a group consisting of: (a) average intensity function; (b) maximum intensity function; and any combination thereof.

The set of vibrations in an octave predicting an impending multisystem failure appears both in an average intensity function and a maximum intensity function (the functions are given above).

In yet another embodiment of the invention, wherein searching the crater feature in a way selected from a group consisting of: (a) manually; (b) automatically; and any combination thereof.

It is possible that the output will be a graph of the intensity function that the person making the diagnosis will interpret and will manually determine the amount of vibrations in an octave and determine whether a person is about to have s multisystem failure. Another possibility is that the output will be an answer whether the person is about to have a multisystem failure or not. The third possibility is that the output will be the number of vibrations per octave (and maybe their slope) and that the person making the diagnosis will determine according to this data whether a person is about to have a multisystem failure.

In yet another embodiment of the invention, additionally comprising a step of graphically plotting the intensity function.

In yet another embodiment of the invention a method for predicting a long term expected multisystem failure in a patient, comprising steps of: (a) obtaining data of recorded speech of the patient; (b) calculating an intensity function of the data across a plurality of frequencies; and (c) searching for at least one crater feature in the intensity function; wherein the method additionally comprising step of: (d) diagnosing the patient with a long term expected multisystem failure according to identification of said at least one crater feature in step (c).

In yet another embodiment of the invention, wherein said multisystem failure is caused by a stroke.

The data may be recorded on a tape, a CD or any type of digital media like a computer, smart-phone or a tablet. A professional recording in a studio with no interruptions background noise is preferable but also a simple home recording in a quite environment will be sufficient for the analysis.

In yet another embodiment of the invention, wherein the crater feature depth is over 30%.

The intensity in the intensity function is a normalized intensity and 100% is defined as the highest intensity identified. All other intensities are in accordance with the highest intensity defined as 100%.

In yet another embodiment of the invention, wherein said crater feature appears in a location in the range of 140-180 Hz and 280-360 Hz.

The method of claim 29, wherein the crater feature has a horizontal base in the range of 180-250 Hz.

In yet another embodiment of the invention, wherein the recorded speech is at least 15 seconds long. It is important that the audible data will include at least 15 second speech of the person to be diagnosed. Shorter segments of speech are also possible but the longer the speech segment the analysis is more accurate.

In yet another embodiment of the invention, wherein additionally comprising a step of selecting the intensity function from a group consisting of: (a) average intensity function; (b) maximum intensity function; and any combination thereof.

In yet another embodiment of the invention, wherein searching the crater feature in a way selected from a group consisting of: (a) manually; (b) automatically; and any combination thereof.

It is possible that the output will be a graph of the intensity function that the person making the diagnosis will interpret and will manually determine the amount of vibrations in an octave and determine whether a person is about to have s multisystem failure. Another possibility is that the output will be an answer whether the person is about to have a multisystem failure or not. The third possibility is that the output will be the number of vibrations per octave (and maybe their slope) and that the person making the diagnosis will determine according to this data whether a person is about to have a multisystem failure.

In yet another embodiment of the invention, additionally comprising a step of graphically plotting the intensity function.

In yet another embodiment of the invention a system for diagnosing a patient for an expected multisystem failure in a patient, comprising: (a) audible data of the patient's speech (b) at least one input apparatus, adapted to receive the audible data; (c) at least one processing apparatus adapted to transfer the audible data to numerical data; the numerical data contains: (i) frequency of the audible data as a function of time; and (ii) the frequency's intensity; and (d) at least one calculating apparatus adapted to calculate a frequency function from the numerical data; wherein more than 4 vibrations in an octave in the frequency function is predictable of an impending multisystem failure.

In yet another embodiment of the invention, wherein said multisystem failure is caused by a stroke.

In yet another embodiment of the invention, additionally comprising at least one output apparatus adapted to provide a graphical presentation of said frequency function.

The whole system can be a computer that is also able to record a patient's speech, analyze it and provide an output in the form of a graph, the form of number of vibrations per octave or in the form of a statement whether the person is about to have a multisystem failure or not.

If the system is not able to record speech it is possible to provide it the audible data either on CD or an external memory device or through the internet.

In yet another embodiment of the invention, wherein the vibration is defined as at least 10% difference in the intensity throughout no more 25 Hz.

In yet another embodiment of the invention, wherein the octaves to be analyzed are selected from a group consisting of: (a) octave between 220-440 Hz; (b) octave between 280-560 Hz; and any combination thereof.

In yet another embodiment of the invention, wherein more than three vibrations per octave are also indicative of an upcoming multisystem failure; the vibrations have a steep slope; said steep slope is about 30%.

In yet another embodiment of the invention, wherein the recorded speech is at least 15 seconds long.

In yet another embodiment of the invention, wherein the intensity function is selected from a group consisting of: (a) average intensity function; (b) maximum intensity function; and any combination thereof.

In yet another embodiment of the invention, wherein at least one input apparatus, at least one processing apparatus, at least one calculating apparatus, at least one output apparatus comprises at least one computer software and at least one computer hardware.

In yet another embodiment of the invention, additionally comprising at least one output apparatus additionally comprising an analyzing apparatus; the apparatus is adapted to determine according to the graphical presentation whether the patient is suspected to have a multisystem failure in the short or long term.

In yet another embodiment of the invention, additionally comprising at least one plotting apparatus adapted to graphically plot the intensity function.

In yet another embodiment of the invention, additionally comprising at least one recognition apparatus, adapted to recognize more than 4 vibrations in an octave.

In yet another embodiment of the invention a system for diagnosing a patient for an expected multisystem failure in a patient, comprising: (a) audible data of the patient's speech; (b) at least one input apparatus, adapted to receive the audible data; (c) at least one processing apparatus adapted to transfer the audible data to numerical data; the numerical data contains: (i) frequency of the audible data as a function of time; and (ii) the frequency's intensity; and (d) at least one calculating apparatus adapted to calculate a frequency function from the numerical data; wherein a crater in the frequency function is predictable of a long term expected multisystem failure.

The whole system can be a computer that is also able to record a patient's speech, analyze it and provide an output in the form of a graph, the form of reporting on a crater feature or in the form of a statement whether the person is about to have a multisystem failure or not.

If the system is not able to record speech it is possible to provide it the audible data either on CD or an external memory device or through the internet.

In yet another embodiment of the invention, wherein said multisystem failure is caused by a stroke.

In yet another embodiment of the invention, additionally comprising at least one output apparatus adapted to provide a graphical presentation of the frequency function.

In yet another embodiment of the invention, wherein the crater feature depth is over 30%.

In yet another embodiment of the invention, wherein the recorded speech is at least 15 seconds long.

In yet another embodiment of the invention, wherein additionally comprising a step of selecting the intensity function from a group consisting of: (a) average intensity function; (b) maximum intensity function; and any combination thereof.

In yet another embodiment of the invention, wherein the at least one input apparatus, at least one processing apparatus, at least one calculating apparatus, at least one output apparatus comprises at least one computer software and at least one computer hardware.

In yet another embodiment of the invention, wherein the crater feature appears in a location in the range of 140-180 Hz; and 280-360 Hz.

In yet another embodiment of the invention, wherein the crater feature has a horizontal base in the range of 180-250 Hz.

In yet another embodiment of the invention, additionally comprising at least one output apparatus; the apparatus is adapted to determine whether the patient is suspected to have a multisystem failure in the long term.

In yet another embodiment of the invention, additionally comprising at least one plotting apparatus adapted to graphically plot the intensity function.

Reference is now made to FIG. 1 which is a schematic flow diagram illustrating in a non-limiting matter a method for diagnosing an impending multisystem failure in a patient (100). In the first step data of recorded speech is obtained (110). It is preferable that the data will include speech length exceeding 15 seconds. The longer the speech time is the more accurate the data analysis is. From the data received an intensity function is obtained across a plurality of frequencies (120). In the last step, the number of vibrations in the range of an octave is determined (130). If there are more than four vibrations in a step there is a high chance for an impending multisystem failure in the person that his speech was analyzed. Also more than three vibrations is a good indication for a pending multisystem failure if their slope is steep. The octaves usually evaluated for their number of peaks are 220-440 Hz and 280-560 Hz.

Figure 2:
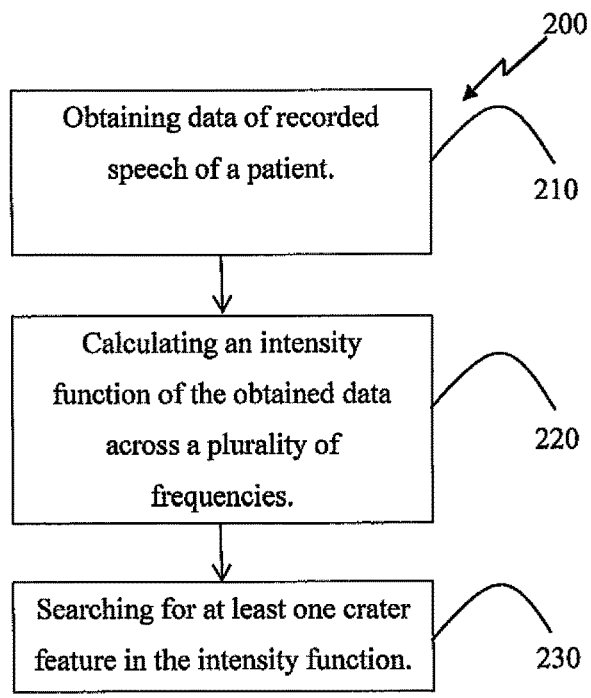
FIG. 2 is a schematic flow diagram illustrating the method for predicting a long term expected multisystem failure in a patient (200)

Reference is now made to FIG. 2 which is a schematic flow diagram illustrating in a non-limiting matter the method for predicting a long term expected multisystem failure in a patient (200). Like the method in FIG. 1 the first step is obtaining audible data (210) from which an intensity function is obtained across a plurality of frequencies (220). In the last step, the function is investigated to find a crater feature (230), especially in the areas of 140-180 Hz and 280-360 Hz. If a crater feature appears in the intensity function there is a strong indication of an expected multisystem failure in the long term.

Figure 3:
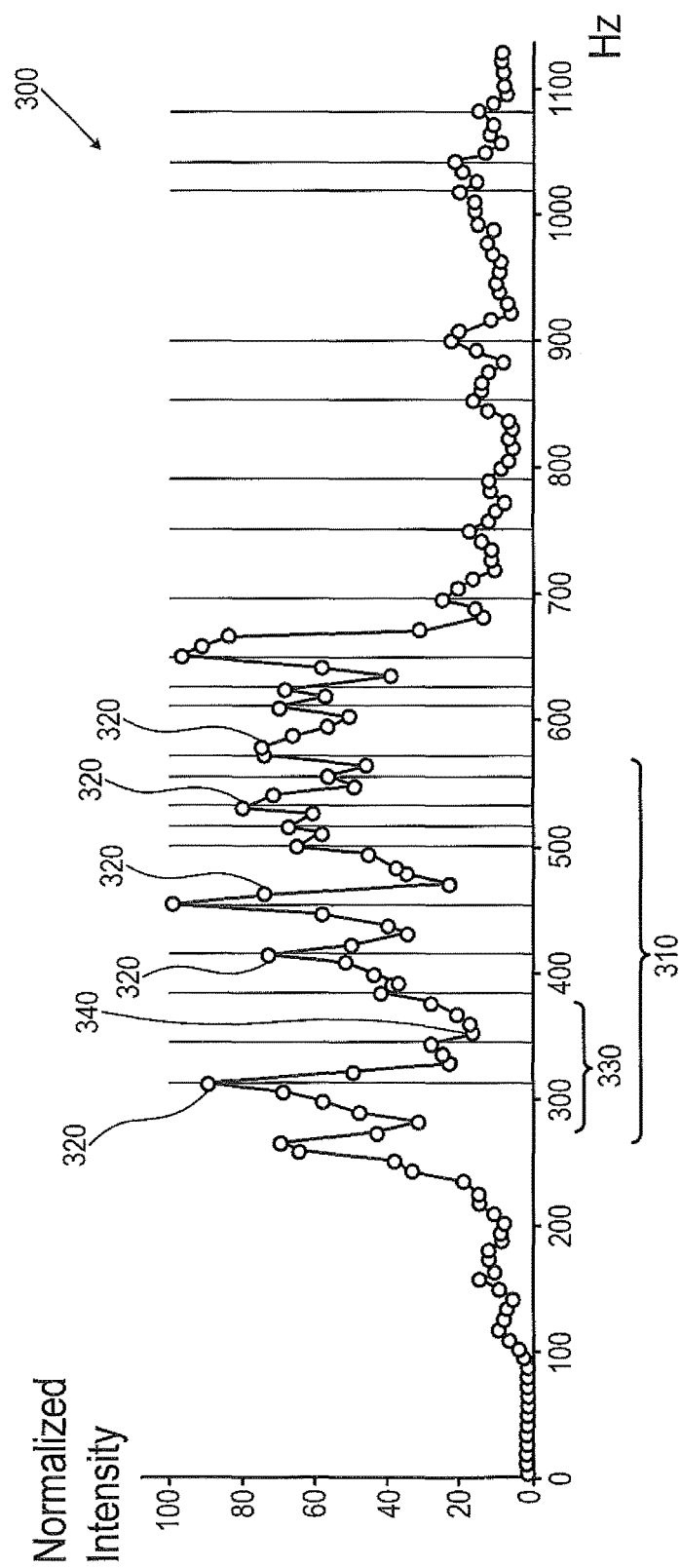
FIGS. 3, 4 and 5 illustrate example graphs of intensity of a voice signal as a function of frequency (300, 400 and 500).
Figure 4:
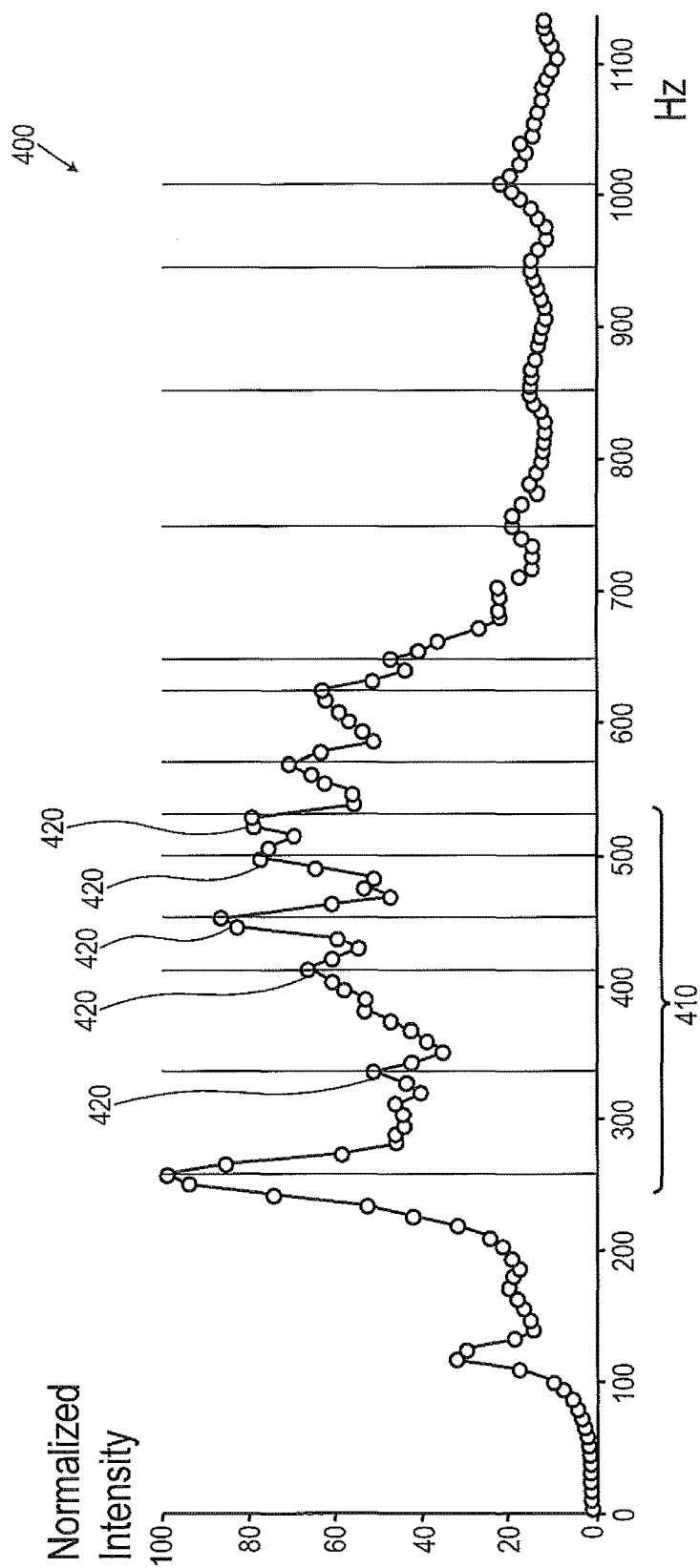
Figure 5:
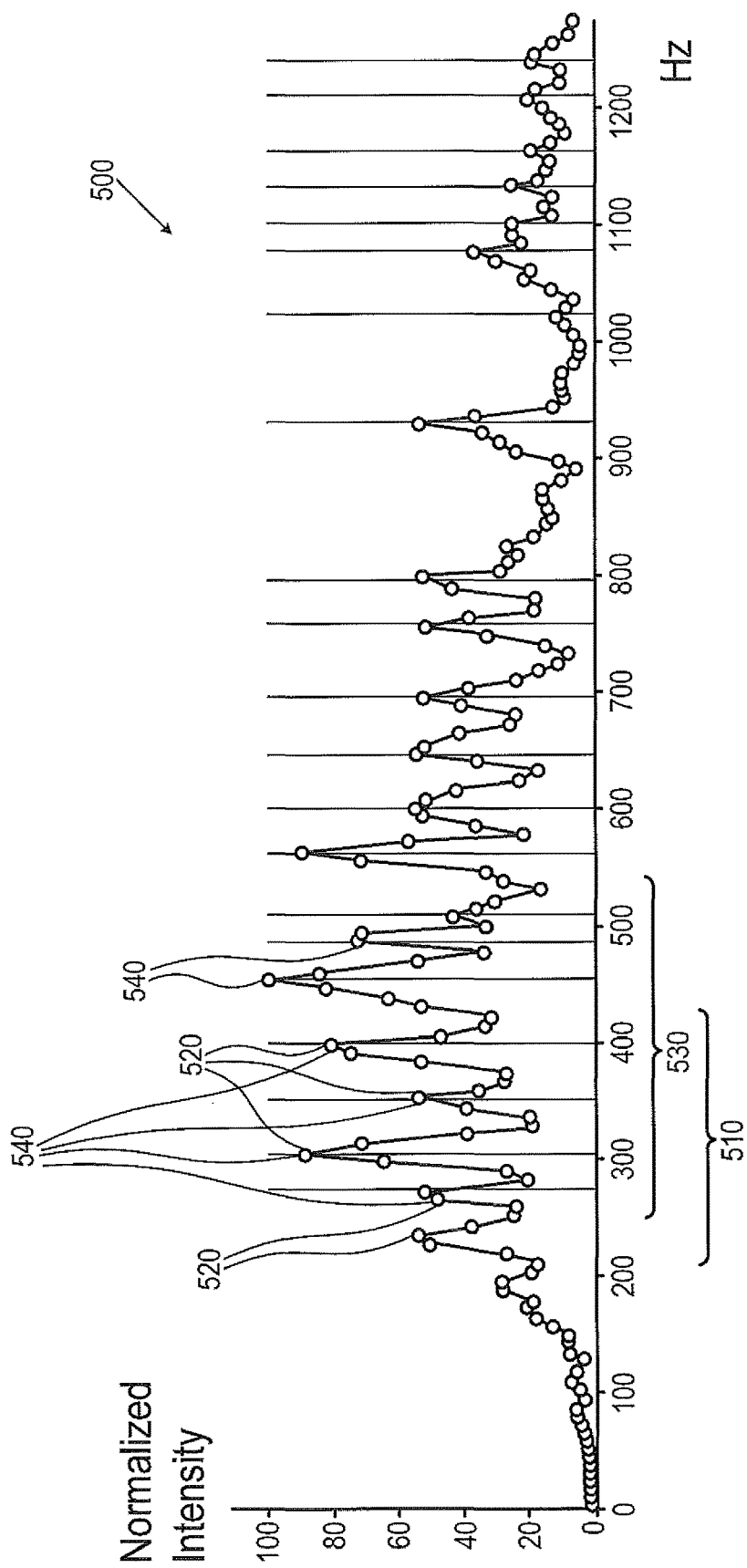

Reference is now made to FIGS. 3, 4 and 5 which illustrate example graphs of intensity of a voice signal as a function of frequency. The audible data was recorded extracted from regular recording of speech. FIG. 3 (300) is an average function that predicts both an impending and a long term expected multisystem failure. The impending multisystem failure can be interpreted from the region of the graph of 280-560 (310) Hz which is an octave with 5 vibrations (320). The long term expected multisystem failure can be interpreted from the region 280-360 Hz (330) that shows a crater feature (340).

FIGS. 4 and 5 are only predictable of a long term expected multisystem failure since they show no crater features. In FIG. 4 (400), which is an average function, we can see in the region of 280-560 Hz (410) five vibrations (420). FIG. 5 (500) is a maximum function of data of speech of a person that had a multisystem failure the day after recording this audible data. We can see both in the region of 220-400 Hz (510) and the region of 280-560 Hz (530) 5 vibrations (520 and 540, respectively).

In some embodiments of the current invention, there is a method for diagnosing an impending multisystem failure in a patient. The method comprising steps of: a. obtaining data of recorded speech by a computer readable medium having instructions thereon; (b) calculating via said instructions an intensity function of the data across a plurality of frequencies; (c) determining the number of vibrations in the range of an octave in the recorded speech via said instructions; wherein the number of vibrations are larger than four is indicative of said impending multisystem failure in said patient.

The invention claimed is:

1. A method for diagnosing an impending multisystem failure in a patient, comprising steps of:
   a. obtaining data of recorded speech of the patient;
   b. calculating a maximum intensity function of the data across a plurality of frequencies; said maximum intensity function defined as a maximum intensity in said recorded speech at each said frequency in said plurality of frequencies; and
   c. counting a number of peaks in a range of an octave in the maximum intensity function of the recorded speech; said peaks defined as having an amplitude of at least 10% of a surrounding baseline value in said maximum intensity function throughout no more 25 Hz;
   wherein an impending multisystem failure is predicted in said patient if said number of peaks is larger than four.

2. The method of claim 1, wherein said multisystem failure is predicted to be caused by a stroke.

3. The method of claim 1, additionally comprising a step of determining said octave to be analyzed from a group consisting of: (a) octave between 220-440 Hz; (b) octave between 280-560 Hz; and any combination thereof.

4. The method of claim 1, wherein more than three peaks per said octave are further predictive of said impending multisystem failure; said peaks have a steep slope; said steep slope is about 30%.

5. The method of claim 1, wherein said recorded speech is at least 15 seconds long.

6. The method of claim 1, wherein determining the number of peaks is in a way selected from a group consisting of: (a) manually; (b) automatically; and any combination thereof.

7. The method of claim 1, additionally comprising a step of graphically plotting said maximum intensity function.

8. A method for predicting a long term expected multisystem failure in a patient, comprising steps of:
   a. obtaining data of recorded speech of the patient;
   b. calculating a maximum intensity function of said data across a plurality of frequencies;
   c. searching for at least one crater feature in said maximum intensity function; said at least one crater feature defined as a shape of said maximum intensity function manifested by a sharp drop at a first frequency followed by a depth of over 30% along approximately 50 Hz or more and then a relatively steep rise at a second frequency; and wherein
   the method additionally comprises the step of:
   d. diagnosing said patient with a long term expected multisystem failure according to identification of said at least one crater feature in step (c).

9. The method of claim 8, wherein said multisystem failure is predicted to be caused by a stroke.

10. The method of claim 8, wherein said searching for at least one crater feature is limited to crater features appearing in a location in the ranges of 140-180 Hz; and 280-360 Hz.

11. The method of claim 8, wherein said at least one crater feature is further defined to have a horizontal base in the range of 180-250 Hz.

12. The method of claim 8, wherein said recorded speech is at least 15 seconds long.

13. The method of claim 8, wherein searching for said at least one crater feature is in a way selected from a group consisting of: (a) manually; (b) automatically; and any combination thereof.

14. The method of claim 8, additionally comprising a step of graphically plotting said average intensity function.

15. A system for diagnosing a patient for an expected multisystem failure in a patient, comprising:
   a. at least one input apparatus, configured to obtain data of recorded speech of said patient;
   b. at least one processing apparatus configured to
      i. calculate a maximum intensity function of the data across a plurality of frequencies; said maximum intensity function defined as a maximum intensity in said recorded speech at each said frequency in said plurality of frequencies; and
      ii. count a number of peaks in a range of an octave in the maximum intensity function of the recorded speech; said peaks counted in said number where a value of said maximum intensity function at a said peak is at least 10% greater than a surrounding baseline value in said maximum intensity function throughout no more 25 Hz;
   wherein an impending multisystem failure is predicted in said patient if said number of peaks is larger than four.

16. The system of claim 15, wherein said multisystem failure is predicted to be caused by a stroke.

17. The system of claim 15, additionally comprising said audible data of said patient's speech.

18. The system of claim 15, additionally comprising at least one output apparatus configured to provide a graphical presentation of said maximum frequency function.

19. The system of claim 15, wherein the octaves to be analyzed are selected from a group consisting of: (a) octave between 220-440 Hz; (b) octave between 280-560 Hz; and any combination thereof.

20. The system of claim 15, wherein more than three peaks per octave are also predictive of an upcoming multisystem failure; said peaks have a steep slope; said steep slope is about 30%.

21. The system of claim 15, wherein said audible data comprises at least 15 seconds of said patient's speech.

22. The system of claim 18, wherein said at least one input apparatus, said at least one processing apparatus, said at least one calculating apparatus, said at least one output apparatus comprises at least one computer software and at least one computer hardware.

23. The system of claim 15, additionally comprising at least one plotting apparatus configured to graphically plot said intensity function.

24. The system of claim 15, additionally comprising at least one output apparatus; said apparatus is configured to determine whether said patient is suspected to have an impending multisystem failure.

25. The system of claim 15, additionally comprising at least one recognition apparatus, configured to recognize said more than 4 peaks in an octave.

26. A system for diagnosing a patient for an expected multisystem failure in a patient, comprising:
   a. at least one input apparatus, configured to receive audible data of said patient's speech;
   b. at least one processing apparatus configured to transfer said audible data to numerical data; said numerical data contains: (i) frequency of the audible data as a function of time; and (ii) the frequency's intensity; and
   c. at least one calculating apparatus configured to calculate a maximum intensity function from said numerical data and search for at least one crater feature in said maximum intensity function; said at least one crater feature as a shape of said maximum intensity function defined as a depth of over 30% along approximately 50 Hz or more and then a relatively steep rise at a second frequency;
   wherein a said at least one crater feature in said maximum intensity function is predictive of a long term expected multisystem failure.

27. The system of claim 26, wherein said multisystem failure is predicted to be caused by a stroke.

28. The system of claim 26, additionally comprising said audible data of said patient's speech.

29. The system of claim 26, additionally comprising at least one output apparatus configured to provide a graphical presentation of said intensity function.

30. The system of claim 26, wherein said audible data comprises at least 15 seconds of said patient's speech.

31. The system of claim 29, wherein said at least one input apparatus, said at least one processing apparatus, said at least one calculating apparatus, said at least one output apparatus comprises at least one computer software and at least one computer hardware.

32. The system of claim 26, wherein said searching for at least one crater feature is limited to crater features appearing in a location in the ranges of 140-180 Hz and 280-360 Hz.

33. The method of claim 26, wherein said at least one crater feature has a horizontal base in the range of 180-250 Hz.

34. The system of claim 26, additionally comprising at least one output apparatus; said apparatus is configured to determine whether said patient is suspected to have a multisystem failure in the long term.

35. The system of claim 26, additionally comprising at least one plotting apparatus configured to graphically plot said intensity function.

36. The system of claim 26, additionally comprising at least one recognition apparatus configured to recognize said at least one crater feature.

37. The method of claim 1, further comprising steps of:
a. calculating a maximum intensity function of said data across said plurality of frequencies;
b. searching for at least one crater feature in said maximum intensity function; said at least one crater feature defined as a shape of said maximum intensity function manifested by a sharp drop at a first frequency followed by a depth of over 30% along approximately 50 Hz or more and then a relatively steep rise at a second frequency; and
c. diagnosing said patient with a long term expected multisystem failure according to identification of said at least one crater feature in step (b).

38. The system of claim 15, wherein:
a. said calculating apparatus is further configured to calculate a maximum intensity function from said numerical data and search for at least one crater feature in said average intensity function; said at least one crater feature defined as a shape of said maximum intensity function manifested by a sharp drop at a first frequency followed by a depth of over 30% along approximately 50 Hz or more and then a relatively steep rise at a second frequency; and
b. a said at least one crater feature in said maximum intensity function is predictive of a long term expected multisystem failure.

* * * * *